(12) United States Patent
O'Connell

(10) Patent No.: US 9,107,967 B2
(45) Date of Patent: Aug. 18, 2015

(54) APPARATUS AND METHOD FOR TREATING STORED CROPS INFECTED WITH TOXINS

(75) Inventor: Thomas W. O'Connell, Palatine, IL (US)

(73) Assignee: Pureline Treatment Systems, LLC, Palatine, IL (US)

(*) Notice: Subject to any disclaimer, the term of this patent is extended or adjusted under 35 U.S.C. 154(b) by 260 days.

(21) Appl. No.: 13/577,259

(22) PCT Filed: Feb. 4, 2011

(86) PCT No.: PCT/US2011/023751
§ 371 (c)(1),
(2), (4) Date: Nov. 13, 2012

(87) PCT Pub. No.: WO2011/100165
PCT Pub. Date: Aug. 18, 2011

(65) Prior Publication Data
US 2013/0071287 A1    Mar. 21, 2013

Related U.S. Application Data

(60) Provisional application No. 61/301,376, filed on Feb. 4, 2010.

(51) Int. Cl.
*A61L 9/00* (2006.01)
*A01M 13/00* (2006.01)
*A61L 2/00* (2006.01)
*A23B 9/18* (2006.01)
*C01B 11/02* (2006.01)

(52) U.S. Cl.
CPC .......... *A61L 2/0094* (2013.01); *A23B 9/18* (2013.01); *C01B 11/024* (2013.01); *C01B 11/026* (2013.01)

(58) Field of Classification Search
CPC ............ A61J 1/00; A61K 8/33; B65D 81/38; A61L 2/00; A61L 9/00; A61L 9/03; C06D 5/00
USPC .............. 422/1, 28, 32, 255, 261, 305–307; 43/125
See application file for complete search history.

(56) References Cited

U.S. PATENT DOCUMENTS

| 6,881,320 B1 * | 4/2005 | Krafton et al. ............... 205/556 |
| 2004/0109799 A1 * | 6/2004 | Kadlec et al. ............... 422/292 |

* cited by examiner

*Primary Examiner* — Monzer R Chorbaji
(74) *Attorney, Agent, or Firm* — Smyrski Law Group, A P.C.

(57) ABSTRACT

A method of reducing toxins in stored crops comprises producing a stream of aqueous or gas $ClO_2$ and exposing the stored crops to the $ClO_2$ wherein the $ClO_2$ kills toxin-producing microorganisms and/or reacts with toxins to reduce the toxins in said stored crops. An apparatus for reducing toxins in stored crops comprises a treatment area for containing the stored crops and a $ClO_2$ generator comprising an inlet for introducing at least one chlorine-containing feed chemical and an outlet for exhausting a stream of aqueous or gas $ClO_2$ from the generator into the treatment area wherein introducing the $ClO_2$ kills toxin-producing microorganisms and/or reacts with toxin molecules to reduce the toxins in the stored crops.

30 Claims, 4 Drawing Sheets

APPARATUS AND METHOD FOR TREATING STORED CROPS INFECTED WITH TOXINS

The present application is a U.S. National Stage Filing pursuant to 35 U.S.C. §371 based on and claiming priority to PCT Application PCT/US2011/023751, entitled "Apparatus and Method For Treating Stored Crops Infected with Toxins," inventor Thomas W. O'Connell, filed 4 Feb. 2011, which claims priority based on U.S. Provisional Patent Application Ser. No. 61/301,376, entitled "Apparatus and Method For Treating Stored Crops Infected with Toxins," inventor Thomas W. O'Connell, filed Feb. 4, 2010, and the disclosures of both applications are incorporated herein by reference.

FIELD OF THE INVENTION

Generally, the technical field involves treating stored crops infected with toxins. Specifically, it is a method and apparatus for reducing the concentration of microorganisms that cause the stored crops to be infected with mycotoxins using chlorine dioxide. Specific contemplated uses include in grain silos, grain storage areas and fermentation plants, such as ethanol and beverage plants. This method offers the benefit of treating both the source of the toxins and the toxins themselves.

BACKGROUND OF THE INVENTION

Some microorganisms (such as molds, fungi or bacteria) grow on crops (including grains) and forages and produce toxins known as mycotoxins. These mycotoxins can be poisonous, mutagenic, teratogenic or carcinogenic when consumed by humans or livestock. Feeds that contain mycotoxins reduce animal productivity and may cause disease or even death.

Mycotoxins are usually found in temperate regions. The microorganisms often propagate in agricultural plants whenever environmental conditional are favorable. Such conditions include cool damp summers, late wet harvests and poor storage after harvest. Where mold growth has occurred it is likely that mycotoxins have been produced.

Mycotoxins can remain in food and feed long after the microorganism that produced them has died. Therefore toxins can be present at potentially dangerous levels in products that are not visibly moldy.

In any given year approximately 20% of all grains harvested become infected with mycotoxins. This infected grain has little value for either human consumption or animal feed. The mycotoxins can be poisonous, mutagenic, teratogenic or carcinogenic to both humans and animals. Mycotoxins can also lower the nutritional value of feed by changing the vitamin and amino acid content. This reduces the energy derived from the feed, which leads to lower feed efficiency. Losses of freshness and palatability results in feed rejection and lower weight gain. Reproduction difficulties of farm animals caused by mycotoxins can also be costly.

There has not previously been a satisfactory method for remedying the problem of mycotoxin infection. Infected crops must be discounted or discarded. Since no acceptable method of dealing with mycotoxins exists, the United States Food and Drug Administration consider mycotoxin infection to be a serious financial and health problem.

SUMMARY OF THE INVENTION

The current method and apparatus uses chlorine dioxide ($ClO_2$) to kill mold, bacteria or other microbiological elements that create toxins, such as mycotoxin and to detoxify the toxins.

One embodiment of the current method of reducing toxin-producing microorganism concentration in stored crops comprises the steps of (a) producing $ClO_2$ gas; and (b) exposing the stored crops to the $ClO_2$ gas wherein the $ClO_2$ gas kills substantially all toxin-producing microorganisms in the stored crops. The steps can be performed sequentially.

The $ClO_2$ gas can be generated in a number of different ways. For example, $ClO_2$ gas can be generated by reacting chlorine gas with water and then adding sodium chlorite, by reacting sodium hypochlorite with an acid and then adding sodium chlorite, by reacting sodium chlorite and hydrochloric acid, using an electrochemical cell and sodium chlorite, using an electrochemical cell and sodium chlorate, using an equipment-based sodium chlorate and hydrogen peroxide method, reacting sodium chlorate and hydrogen peroxide, or by dry mix chlorine dioxide packets having a chlorite precursor packet and an acid activator packet.

In one embodiment the toxin-producing organisms can produce mycotoxins. Examples of mycotoxins include, Aflatoxin, Vomitoxin, Fumonisin, Ochratoxin, T-2 Toxin, Zearalenone, Fusarochromanone, Patulin and Citrinin.

The stored crops can be a number of different crops. For example, the stored crops could be stored grains that are stored and treated in a grain silo or a grain dryer. The stored crops could also be stored corn that is stored and treated in an ethanol plant.

Additional compositions could also be applied to the stored grains. For example, the method could further comprise exposing the stored crops to citric acid wherein the citric acid kills toxin-producing microorganisms in the stored crops.

Another embodiment of the method of reducing toxin molecule concentration in stored crops comprises the steps of (a) producing $ClO_2$ gas; and (b) exposing the stored crops to the $ClO_2$ gas wherein the $ClO_2$ gas reacts with the molecules to detoxify the toxins. The steps can be performed sequentially. The $ClO_2$ gas can be generated in a number of different ways including those outlined above.

In one embodiment the toxins can be mycotoxins. Examples of mycotoxins include, Aflatoxin, Vomitoxin, Fumonisin, Ochratoxin, T-2 Toxin, Zearalenone, Fusarochromanone, Patulin and Citrinin.

The stored crops can be a number of different crops. For example, the stored crops could be stored grains that are stored and treated in a grain silo or a grain dryer. The stored crops could also be stored corn that is stored and treated in an ethanol plant.

Additional compositions could also be applied to the stored grains. For example, the method could further comprise exposing the stored crops to citric acid wherein the citric acid reacts with the molecules to detoxify the toxins.

Another embodiment of the current method of reducing toxin-producing microorganism concentration in stored crops comprises the steps of (a) producing an aqueous $ClO_2$ solution; and (b) exposing the stored crops to the aqueous $ClO_2$ solution wherein the aqueous $ClO_2$ solution kills substantially all toxin-producing microorganisms in the stored crops. The steps can be performed sequentially. The $ClO_2$ gas can be generated in a number of different ways including those outlined above.

The aqueous $ClO_2$ solution could be produced in a number of different ways. For example, the aqueous $ClO_2$ could be produced by a solid composition comprising an alkali chlorite salt, a solid acid source and an acrylate. As another example, the aqueous $ClO_2$ could also be produced using a chlorine dioxide solution generator.

In one embodiment the toxin-producing organisms can produce mycotoxins. Examples of mycotoxins include, Aflatoxin, Vomitoxin, Fumonisin, Ochratoxin, T-2 Toxin, Zearalenone, Fusarochromanone, Patulin and Citrinin.

The stored crops can be a number of different crops. For example, the stored crops could be stored grains that are stored and treated in a grain silo or a grain dryer. The stored crops could also be stored corn that is stored and treated in an ethanol plant.

Additional compositions could also be applied to the stored grains. For example, the method could further comprise exposing the stored crops to citric acid wherein the citric acid kills toxin-producing microorganisms in the stored crops.

Another embodiment of the method of reducing toxin molecule concentration in stored crops comprises the steps of (a) producing an aqueous $ClO_2$ solution; and (b) exposing the stored crops to the aqueous $ClO_2$ solution wherein the aqueous $ClO_2$ solution reacts with the molecules to detoxify the toxins. The steps can be performed sequentially. The $ClO_2$ gas can be generated in a number of different ways including those outlined above.

The aqueous $ClO_2$ solution could be produced in a number of different ways. For example, the aqueous $ClO_2$ could be produced by a solid composition comprising an alkali chlorite salt, a solid acid source and an acrylate. As another example, the aqueous $ClO_2$ could also be produced using a chlorine dioxide solution generator.

In one embodiment the toxins can be mycotoxins. Examples of mycotoxins include, Aflatoxin, Vomitoxin, Fumonisin, Ochratoxin, T-2 Toxin, Zearalenone, Fusarochromanone, Patulin and Citrinin.

The stored crops can be a number of different crops. For example, the stored crops could be stored grains that are stored and treated in a grain silo or a grain dryer. The stored crops could also be stored corn that is stored and treated in an ethanol plant Additional compositions could also be applied to the stored grains. For example, the method could further comprise exposing the stored crops to citric acid wherein the citric acid reacts with the molecules to detoxify the toxins.

An apparatus for reducing toxins in stored crops comprises a treatment area for containing the stored crops and a $ClO_2$ generator comprising an inlet for introducing at least one chlorine-containing feed chemical and an outlet for exhausting a $ClO_2$ gas stream from the generator into the treatment area wherein introducing the $ClO_2$ gas kills toxin-producing microorganisms and reacts with toxins reduce the toxins in the stored crops. The $ClO_2$ generator can be mobile.

In one embodiment the toxins can be mycotoxins. Examples of mycotoxins include, Aflatoxin, Vomitoxin, Fumonisin, Ochratoxin, T-2 Toxin, Zearalenone, Fusarochromanone, Patulin and Citrinin.

The stored crops can be a number of different crops. For example, the stored crops could be stored grains that treatment area can be a grain silo or a grain dryer. The stored crops could also be stored corn and the treatment area could be a vessel in an ethanol plant.

Another apparatus for reducing toxins in stored crops comprises a treatment area for containing the stored crops and a $ClO_2$ generator comprising an inlet for introducing at least one chlorine-containing feed chemical and an outlet for exhausting an aqueous $ClO_2$ stream from the generator into the treatment area wherein introducing the aqueous $ClO_2$ stream kills toxin-producing microorganisms and reacts with toxins reduce the toxins in the stored crops. The $ClO_2$ generator can be mobile.

In one embodiment the toxins can be mycotoxins. Examples of mycotoxins include, Aflatoxin, Vomitoxin, Fumonisin, Ochratoxin, T-2 Toxin, Zearalenone, Fusarochromanone, Patulin and Citrinin.

The stored crops can be a number of different crops. For example, the stored crops could be stored grains that treatment area can be a grain silo or a grain dryer. The stored crops could also be stored corn and the treatment area could be a vessel in an ethanol plant.

These and other features of the present method and apparatus are discussed or apparent in the following detailed description.

DETAILED DESCRIPTION OF PREFERRED EMBODIMENT(S)

Figure 1:
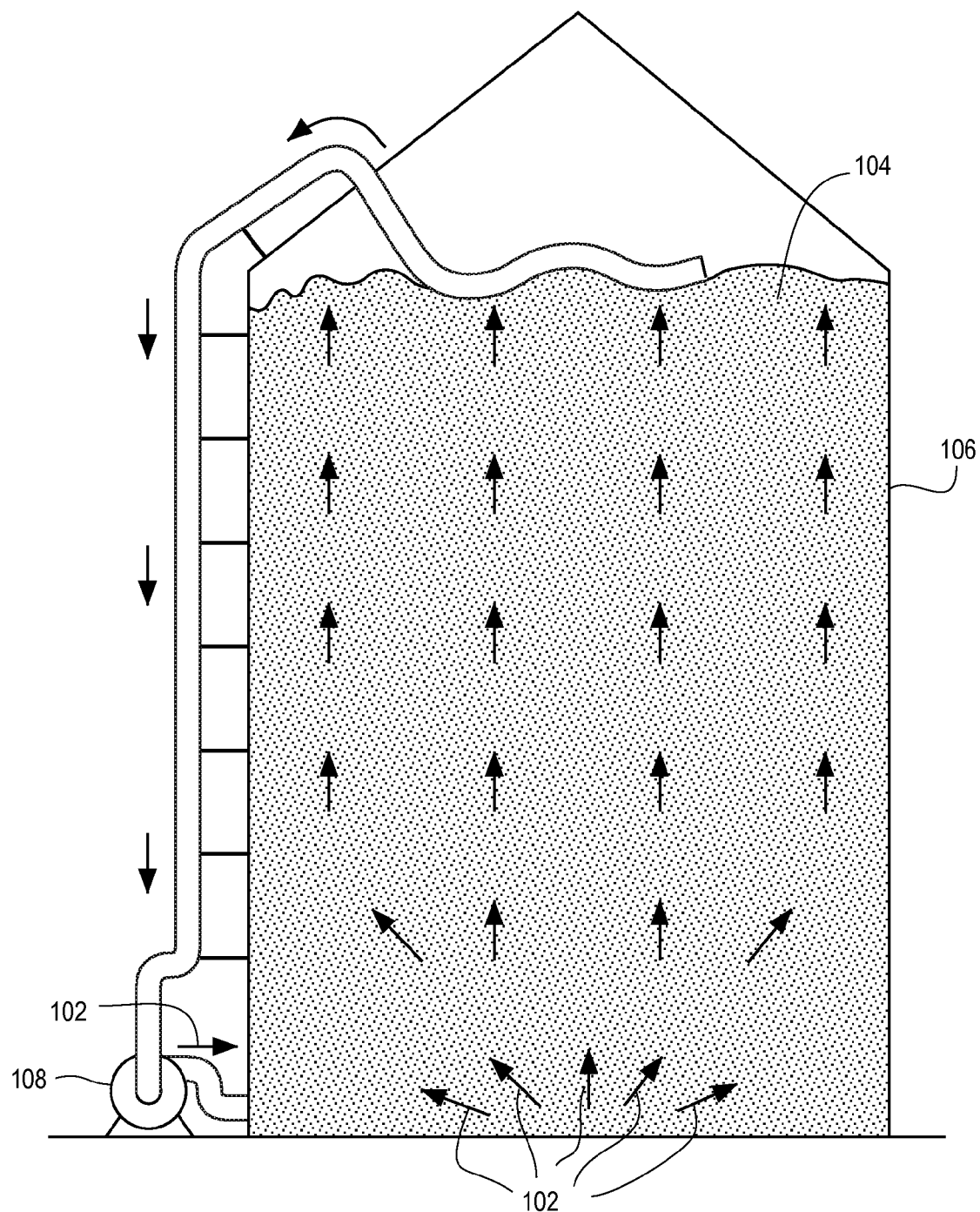
FIG. 1 is an illustration of an embodiment of the present method of reducing toxins and/or toxin-producing microorganisms in stored grains using chlorine dioxide in a silo.

The current disclosure relates to treating stored crops infected with toxins. Specifically, it is a method and apparatus for reducing the concentration of microorganisms that cause the stored crops to be infected with mycotoxins using chlorine dioxide. Specific contemplated uses include in grain silos, grain storage areas and fermentation plants, such as ethanol and beverage plants. This method offers the benefit of treating both the source of the toxins and the toxins themselves.

As discussed above, some microorganisms (such as molds, fungi or bacteria) grow on crops and forages and produce toxins known as mycotoxins. These mycotoxins can be poisonous, mutagenic, teratogenic or carcinogenic when consumed by humans or livestock. Once grain is infected it has little value for either human consumption or animal feed.

Mycotoxins can affect a large variety of crops. A non-exhaustive list of exemplary crops that can be affected includes corn, milo, nuts, cotton, wheat, barley, oats, rice, coffee, cocoa, raisins, apricots, figs and their cellulosic byproducts. Particular attention will be given to grains in this application. However, the apparatus and method are designed to apply to numerous different crops.

The present method and apparatus can be used to treat a variety of different types of microorganism-produced toxins and the toxins they produce. The toxins could be produced by molds, fungi, bacteria and other microbiological elements. Mycotoxins are one particular type of toxin. Mycotoxins are produced by molds and fungi. Examples of mycotoxins include Aflatoxin, Deoxynivalenol (also known as Vomitoxin or DON), Fumonisin (also known as B-1 Toxin), Ochratoxin, T-2 Toxin, Zearalenone (also known as F-2), Fusarochromanone, Patulin and Citrinin. The present apparatus and method are effective against these mycotoxins, other mycotoxins and other microorganism-produced toxins not specifically identified here.

Chlorine dioxide ($ClO_2$) has many industrial and municipal uses. When produced and handled properly, $ClO_2$ is an effective and powerful biocide, disinfectant and oxidizer. $ClO_2$ has been used as a disinfectant in the food and beverage industries, wastewater treatment, industrial water treatment, cleaning and disinfections of medical wastes, textile bleaching, odor control for the rendering industry, circuit board cleansing in the electronics industry, and uses in the oil and gas industry. It is an effective biocide at low concentrations and over a wide pH range. $ClO_2$ is desirable because when it reacts with an organism, it reduces to chlorite ion and then to chloride, which studies to date have shown does not pose a significant adverse risk to human health. The use of chlorine, on the other hand, can result in the creation of chlorinated organic compounds when treating water. Chlorinated compounds are suspected to increase cancer risk.

The current method and apparatus involve deploying aqueous or gaseous $ClO_2$ into grains or other crops affected by toxins, such as mycotoxins. Examples of potential uses are in grain silos, grain dryers and fermentation plants, such as ethanol and beverage plants.

FIGS. 1-4 show illustrations of the present method of reducing toxins and/or toxin-producing microorganisms in stored crops using chlorine dioxide in a grain silo, a grain drier and an ethanol plant, respectively. In FIG. 1 gaseous or aqueous chlorine dioxide 102 is applied to grain 104 in a grain silo 106. As one example, this is done via a blower inlet 108 in the silo, as shown.

Figure 2:
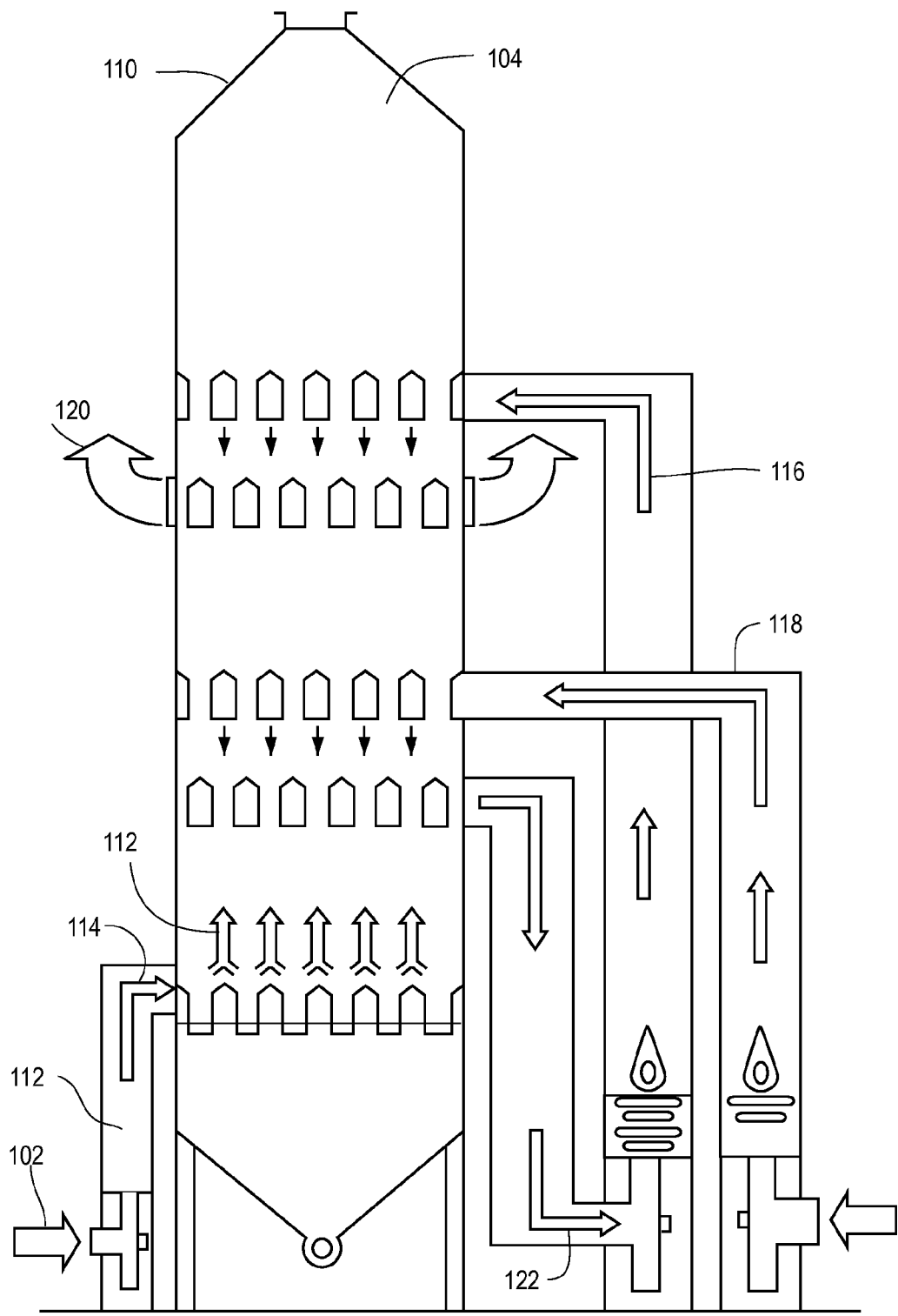
FIG. 2 is an illustration of another embodiment of the present method of reducing toxins and/or toxin-producing microorganisms in stored grains using chlorine dioxide in a grain dryer.

In FIG. 2 gaseous or aqueous chlorine dioxide 102 is applied to grain 104 in a grain dryer 110. As one example, this is done via the cooling air 112 inlet 114, as shown. Gaseous or aqueous chlorine dioxide 102 could also be applied with the first stage drying air 116 or second and third stage drying air 118. Gaseous or aqueous chlorine dioxide 102 could exit with the saturated exhaust air 120 or recycled exhaust air 122.

Figure 3:
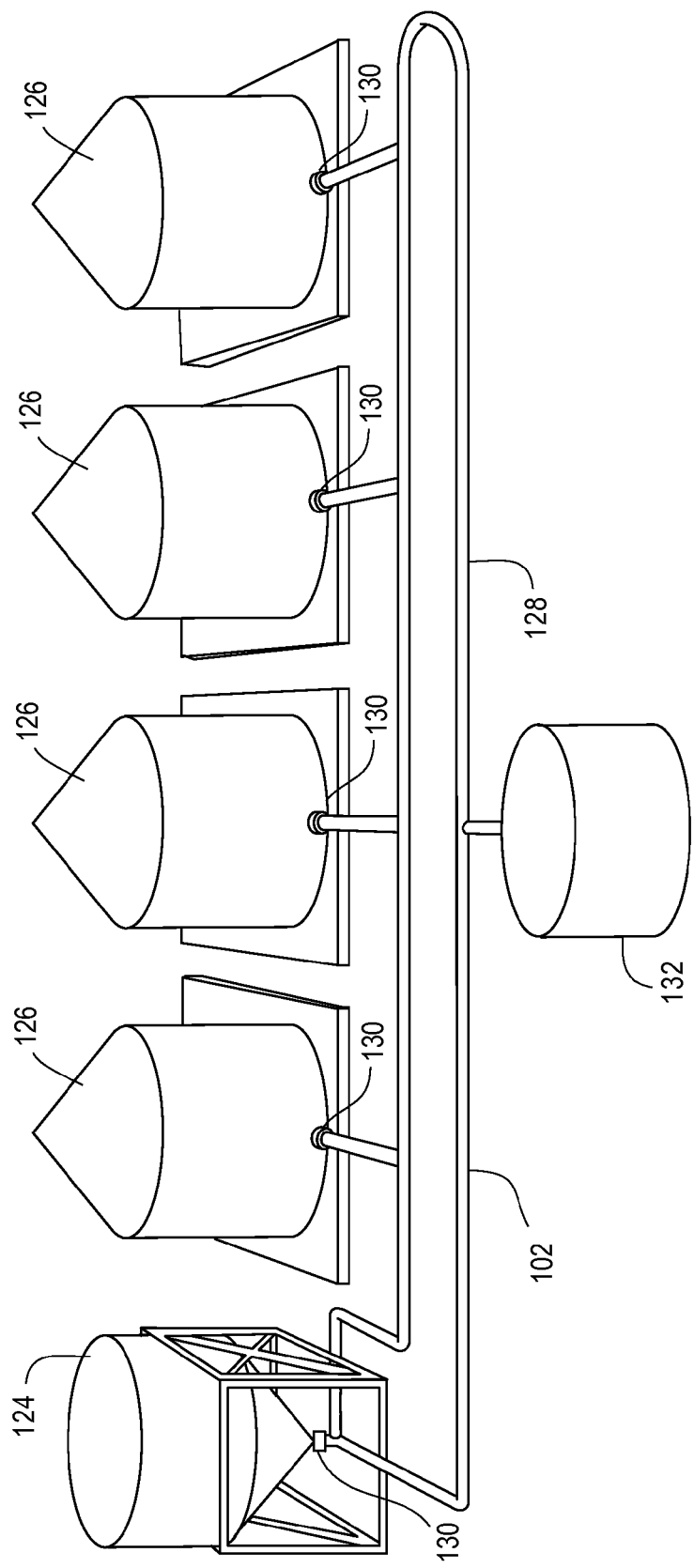
FIG. 3 is an illustration of another embodiment of the present method of reducing toxins and/or toxin-producing microorganisms in stored corn using chlorine dioxide in an ethanol plant.

In FIG. 3 chlorine dioxide is applied to an ethanol plant. As one example, gaseous or aqueous chlorine dioxide 102 is introduced into the yeast propagation tank(s) 124 and/or the fermentation tank(s) 126 via piping 128 and valves 130, as shown. The gaseous chlorine dioxide can be stored in a chlorine dioxide storage vessel 132.

Figure 4:
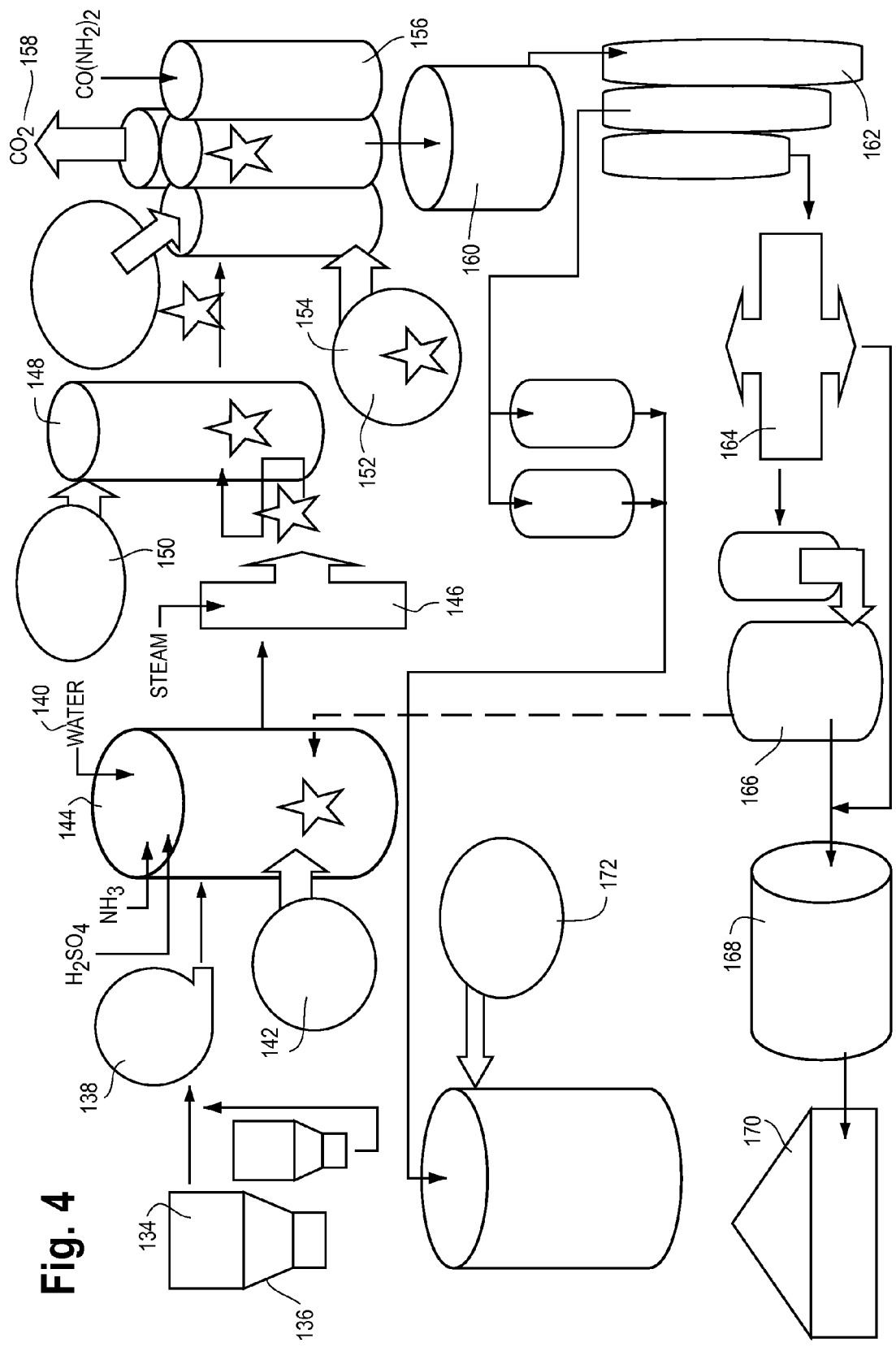
FIG. 4 is an illustration of another embodiment of the present method of reducing toxins and/or toxin-producing microorganisms in stored corn using chlorine dioxide in an ethanol plant.

In FIG. 4 chlorine dioxide is applied to an ethanol plant. The production of fuel ethanol by yeast fermentation is used as an example. However, this is merely one illustration and should not be understood as a limitation. Other fermentation products could include distilled spirits, beer, wine, pharmaceuticals, pharmaceutical intermediates, baking products, nutraceuticals (foodstuff that provides health benefits, such as fortified foods and dietary supplements), nutraceutical intermediates and enzymes. The current method could also be utilized to treat yeast used in the baking industry. Other fermenting microorganisms could also be substituted such as the fungi and bacteria typically used in cellulosic ethanol production, *Trichoderma reesei, Trichoderma viride*, and *Clostridium Ijungdahlii*.

The fermentation process begins with the preparation of a fermentable carbohydrate. In ethanol production, corn 134 is one possible fermentable carbohydrate. Other carbohydrates including cereal grains and cellulose-starch bearing materials, such as wheat or milo, could also be substituted. Cellulosic biomass such as straw and cornstalks could also be used. Cellulosic ethanol production has recently received attention because it uses readily available nonfood biomass to form a valuable fuel. The fermentable carbohydrate is collected in a hopper 136.

In corn-based ethanol production the corn is ground into a fine powder called meal in a hammer mill 138. The meal is then mixed with water 140 and enzymes 142, such as alpha-amylase in a slurry tank 144. The meal is then passed through a cooker 146 into a liquefaction chamber 148 order to liquefy the starch. A product known as corn mash results.

A secondary enzyme 150, such as glucoamylase, will also be added to the mash to convert the liquefied starch into a fermentable sugar. The glucoamylase cleaves single molecules of glucose from the short chain starches, or dextrins. The glucose molecules can then be converted into ethanol during fermentation.

Yeast 152, small microorganisms capable of fermentation, will also be added to the corn mash from a yeast propagation chamber 154. Yeast are fungi that reproduce by budding or fission. One common type of yeast is *Saccharomyces cerevisia*, the species predominantly used in baking and fermentation. Non-*Sacharomyces* yeasts, also known as non-conventional yeasts, are naturally occurring yeasts that exhibit properties that differ from conventional yeasts. Non-conventional yeasts are utilized to make a number of commercial products such as amino acids, chemicals, enzymes, food ingredients, proteins, organic acids, nutraceuticals, pharmaceuticals, cosmetics, polyols, sweeteners and vitamins. Some examples of non-conventional yeasts include *Kuyberomyces lactis, Yarrowia lipolytica, Hansenula polymorphs* and *Pichia pastoris*. The current methods and apparatus are applicable to intermediates and products of both *Sacharomyces* and non-conventional yeast.

Most of the yeast used in fuel ethanol plants and other fermentation processes are purchased from manufacturers of specialty yeast. The yeast are manufactured through a propagation process and usually come in one of three forms: yeast slurry, compressed yeast or active dry yeast. Propagation involves growing a large quantity of yeast from a small lab culture of yeast. During propagation the yeast are provided with the oxygen, nitrogen, sugars, proteins, lipids and ions that are necessary or desirable for optimal growth through aerobic respiration.

Once at the distillery, the yeast may undergo conditioning. The objectives of both propagation and conditioning are to deliver a large volume of yeast to the fermentation tank with high viability, high budding and a low level of infection by other microorganisms. However, conditioning is unlike propagation in that it does not involve growing a large quantity from a small lab culture. During conditioning, conditions are provided to re-hydrate the yeast, bring them out of hibernation and allow for maximum anaerobic growth and reproduction.

Following propagation or conditioning, the yeast enter the fermentation process. The glucoamylase enzyme and yeast are often added into the fermentation tank 156 through separate lines as the mash is filling the fermentation tank. This process is known as simultaneous saccharification and fermentation or SSF. The yeast produce energy by converting the sugars, such as glucose molecules, in the corn mash into carbon dioxide 158 and ethanol.

The fermentation mash, now called "beer" 160 is distilled in a distillation system 162. This process removes the 190 proof ethanol, a type of alcohol, from the solids, which are known as whole stillage 124. These solids are then go through a centrifuge 164 to get wet distillers grains and thin stillage. The distillers grains can be dried in a drum dryer 168 and are highly valued livestock feed ingredients known as dried distillers grains (DDGS) 170. The thin stillage can be evaporated 166 to leave a syrup. After distillation, the alcohol is passed through a dehydration system to remove remaining water. At this point the product is 200 proof ethanol. This ethanol is then denatured 172 by adding a small amount of denaturant, such as gasoline, to make it unfit for human consumption.

During this process gaseous or aqueous chlorine dioxide can be added at a variety of points to treat the grains. For example, gaseous or aqueous chlorine dioxide can be applied to the slurry tank, the cooker, the liquefaction tank, the yeast propagation tank, the fermentor and piping in between the various apparatuses.

Applicants conducted a study in order to determine the effects of $ClO_2$ on toxins. Applicants obtained corn infected with mycotoxins and mycotoxin-producing microorganisms. Applicants exposed the corn kernels to an aqueous $ClO_2$ solution with a concentration of 400 ppm for two hours. Applicants drained the aqueous $ClO_2$ solution from the corn. Applicants ground the corn and tested for the presence of mycotoxins. Applicants also ground untreated corn from the batch and tested that corn for the presence of mycotoxins. Applicants found that the treated corn had a concentration of Vomitoxin of 2.3 ppm and that the untreated corn had a concentration of Vomitoxin of 9 ppm.

Applicants conducted another study in order to determine the effects of $ClO_2$ on toxins. Applicants obtained corn infected with mycotoxins and mycotoxin-producing microorganisms. Applicants ground the corn kernels and mixed them with water to form a mash, similar to what is used in various fermentation plants. Applicants heated an aqueous $ClO_2$ solution with a concentration of 200 ppm to 185° F. Applicants then exposed the mash to the heated aqueous chlorine dioxide solution for two hours. Applicants drained the aqueous $ClO_2$ solution from the mash. Applicants tested the mash for the presence of mycotoxins. Applicants also tested untreated mash from the same batch for the presence of mycotoxins. Applicants found that the treated corn had a concentration of Vomitoxin of 0.5 ppm and that the untreated corn had a concentration of Vomitoxin of 12 ppm.

Thus, Applicants tests proved that $ClO_2$ is effective in reducing the concentration of toxins, such as mycotoxins. It is believed that the $ClO_2$ is able to destroy the toxin-producing microorganisms and treat the toxins themselves simultaneously. The $ClO_2$ is believed to remedy the toxins using a two-fold solution. First, the $ClO_2$ reacts with the toxins to reduce their concentration. The $ClO_2$ also kills microorganisms, such as molds, fungi and bacteria, that produce the toxins.

Aqueous $ClO_2$ can be used for the present method. A number of methods of making aqueous $ClO_2$ are known and can be used in the present application. As a single, non-limiting example a non-equipment based method can be used such as the one discussed in U.S. patent application Ser. No. 11/854, 434. As another non-limiting example, the generator based technology discussed in U.S. patent application Ser. Nos. 10/902,681, 11/145,398, 11/289,813 and 11/458,611 can be used. Each of these applications is incorporated in its entirety.

During processing of certain grains, such as wheat, a sweating or tempering step is used. During this step, the grain is contacted with water. The grain can be contacted with water for various amounts of time. In some examples the contacting occurs over night, in other examples the contacting occurs from 12-24 hours. This can be used as an opportunity the introduce an aqueous $ClO_2$ solution.

Applicants conducted a study where a 75 ppm aqueous $ClO_2$ solution was applied to wheat during tempering or sweating. The aqueous $ClO_2$ solution was applied to the wheat for 12 hours. Prior to the application of the aqueous $ClO_2$ solution, the wheat had a concentration of Vomitoxin of approximately 12 ppm. After the application of the aqueous $ClO_2$ solution, the wheat had a concentration of Vomitoxin of approximately 1 ppm.

Producing $ClO_2$ gas for use in treatment processes is also desirable because there is greater assurance of $ClO_2$ purity when in the gas phase. Pure or substantially pure $ClO_2$ is desirable because it allows the user to precisely maintain the amount of $ClO_2$ added to the stored crops. (The single term "pure" will be used hereinafter to mean either pure or substantially pure.) Addition of pure $ClO_2$ allows the user to carefully monitor and adjust the amount of $ClO_2$ added to the grains or crops. This enables the user to add adequate $ClO_2$ to kill the toxin-producing microorganisms.

Gaseous $ClO_2$ is also desirable for the current method because of its easy application to large areas of affected grains or crops. Gaseous $ClO_2$ can be easily applied to a large area. This allows for treatment of the surface, center and backside of the affected grains Or crops.

$ClO_2$ is, however, unstable in the gas phase and will readily undergo decomposition into chlorine gas ($Cl_2$), oxygen gas ($O_2$), and heat. The high reactivity of $ClO_2$ generally requires that it be produced and used at the same location.

There are a number of methods of producing $ClO_2$ gas which are known to persons familiar with the technology involved here. One or more of these methods can be used. Here are some exemplary methods of producing $ClO_2$ gas. $ClO_2$ gas can be produced using electrochemical cells and a sodium chlorite ($ClO_2$) or chlorate ($ClO_3$) solution. An equipment based sodium chlorate/hydrogen peroxide method also exists. Alternatively, non-equipment based binary, multiple precursor dry or liquid precursor technologies can be used. Examples of non-equipment based methods of $ClO_2$ generation include dry mix chlorine dioxide packets that include both a chlorite precursor packet and an acid activator packet. Other such processes include, but are not limited to, acidification of sodium chlorite, oxidation of chlorite by chlorine, oxidation of chlorite by persulfate, use of acetic anhydride on chlorite, use of sodium hypochlorite and sodium chlorite, use of dry chlorine/chlorite, reduction of chlorates by acidification in the presence of oxalic acid, reduction of chlorates by sulfur dioxide, and the ERCO R-2®, R-3®, R-5®, R-8®, R-10® and R-11® processes, from which $ClO_2$ is generated from $NaClO_3$ in the presence of NaCl and $H_2SO_4$ (R-2 and R-3 processes), from $NaClO_3$ in the presence of HCl (R-5 process), from $NaClO_3$ in the presence of $H_2SO_4$ and $CH_3OH$ (R-8 and R-10 processes), and from $NaClO_3$ in the presence of $H_2O_2$ and $H_2SO_4$ (R-11 process).

Here, three methods will illustrate some possibilities. In the first method, chlorine reacts with water to form hypochlorous acid and hydrochloric acid. These acids then react with sodium chlorite to form chlorine dioxide, water and sodium chloride. In a second method, sodium hypochlorite is combined with hydrochloric or other acid to form hypochlorous acid. Sodium chlorite is then added to this reaction mixture to produce chlorine dioxide. The third method combines sodium chlorite and sufficient hydrochloric acid.

Additional ingredients can also be added with the chlorine dioxide. In one embodiment citric acid can be added to obtain greater reduction in toxin concentration.

The current apparatus comprises a treatment area and a $ClO_2$ generator. The $ClO_2$ generator should also have an outlet for exhausting a $ClO_2$ stream from the generator into the treatment area. The $ClO_2$ stream can be either aqueous or gaseous.

In one embodiment, the ClO$_2$ generator has an input for electricity. There is also an inlet for at least one chlorine containing chemical. There are three different types of chemical feed systems: a vacuum system, a pressure system and a combination system. Many types of feed systems can be employed to deliver chemicals in a fluid state. Chlorine gas, for example, can be added by a vacuum or combination feed system.

In one embodiment the ClO$_2$ generator is an electrochemical generator. The electrochemical generator comprises an anolyte loop and a catholyte loop. The purpose of the anolyte loop is to produce a chlorine dioxide (ClO$_2$) gas by oxidation of chlorite or chlorate, and the process can be referred to as a ClO$_2$ gas generator loop. The ClO$_2$ gas generator loop is essentially a ClO$_2$ gas source. Various sources of ClO$_2$ are available and known in the water treatment field. The catholyte loop of the ClO$_2$ gas generator loop produces sodium hydroxide and hydrogen gas by reduction of water. The process can be operated through a program logic control (PLC) system that can include displays.

Mobile equipment is sometimes desired. This allows the equipment to be manufactured off site, shipped to the desired location, utilized and then removed. This provides ease in transportation, faster erection and commissioning. The ClO$_2$ generator can be made in a mobile fashion.

While particular elements, embodiments and applications of the present invention have been shown and described, it will be understood, of course, that the invention is not limited thereto since modifications can be made by those skilled in the art without departing from the scope of the present disclosure, particularly in light of the foregoing teachings.

What is claimed is:

1. A method of reducing toxin-producing microorganism concentration in stored crops, the method comprising:
   (a) producing ClO$_2$ gas; and
   (b) exposing said stored crops to said ClO$_2$ gas and citric acid at concentrations sufficient to reduce toxin concentrations in the stored crops by at least 74.45 percent;
   wherein said ClO$_2$ gas and citric acid kill toxin-producing microorganisms in said stored crops.

2. The method of claim 1 wherein said steps are performed sequentially.

3. The method of claim 1 wherein said ClO$_2$ gas is generated by reacting chlorine gas with water and then adding sodium chlorite.

4. The method of claim 1 wherein said ClO$_2$ gas is generated by reacting sodium hypochlorite with an acid and then adding sodium chlorite.

5. The method of claim 1 wherein said ClO$_2$ gas is generated by reacting sodium chlorite and hydrochloric acid.

6. The method of claim 1 wherein said ClO$_2$ gas is generated using an electrochemical cell and sodium chlorite.

7. The method of claim 1 wherein said ClO$_2$ gas is generated using an electrochemical cell and sodium chlorate.

8. The method of claim 1 wherein said ClO$_2$ gas is generated using an equipment-based sodium chlorate and hydrogen peroxide method.

9. The method of claim 1 wherein said ClO$_2$ is produced by reacting sodium chlorate and hydrogen peroxide.

10. The method of claim 1 wherein said ClO$_2$ is produced by dry mix chlorine dioxide packets having a chlorite precursor packet and an acid activator packet.

11. The method of claim 1 wherein said toxin-producing organisms produce mycotoxins.

12. The method of claim 11 wherein said mycotoxins are selected from the group comprising Aflatoxin, Vomitoxin, Fumonisin, Ochratoxin, T-2 Toxin, Zearalenone, Fusarochromanone, Patulin and Citrinin.

13. The method of claim 1 wherein said stored crops are stored grains.

14. The method of claim 13 wherein said stored grains are stored and treated in a grain silo.

15. The method of claim 13 wherein said stored grains are stored and treated in a grain dryer.

16. The method of claim 1 wherein said stored crops are stored corn.

17. The method of claim 16 wherein said stored corn is stored and treated in an ethanol plant.

18. The method of claim 1 further comprising exposing said stored crops to citric acid wherein said citric acid kills toxin-producing microorganisms in said stored crops.

19. A method of reducing toxin-producing microorganism concentration in stored crops, the method comprising:
   (a) producing an aqueous ClO$_2$ solution; and
   (b) exposing said stored crops to said aqueous ClO$_2$ solution and citric acid at concentrations sufficient to reduce toxin concentrations in the stored crops by at least 74.45 percent;
   wherein said aqueous ClO$_2$ solution and citric acid kill substantially all toxin-producing microorganisms in said stored crops.

20. The method of claim 19 wherein said steps are performed sequentially.

21. The method of claim 19 wherein said aqueous ClO$_2$ is produced by a solid composition comprising an alkali chlorite salt, a solid acid source and an acrylate.

22. The method of claim 19 wherein said aqueous ClO$_2$ is produced using a chlorine dioxide solution generator.

23. The method of claim 19 wherein said toxin-producing organisms produce mycotoxins.

24. The method of claim 23 wherein said mycotoxins are selected from the group comprising Aflatoxin, Vomitoxin, Fumonisin, Ochratoxin, T-2 Toxin, Zearalenone, Fusarochromanone, Patulin and Citrinin.

25. The method of claim 19 wherein said stored crops are stored grains.

26. The method of claim 25 wherein said stored grains are stored and treated in a grain silo.

27. The method of claim 25 wherein said stored grains are stored and treated in a grain dryer.

28. The method of claim 19 wherein said stored crops are stored corn.

29. The method of claim 28 wherein said stored corn is stored and treated in an ethanol plant.

30. The method of claim 19 further comprising exposing said stored crops to citric acid wherein said citric acid kills toxin-producing microorganisms in said stored crops.

* * * * *